United States Patent [19]

Persinger

[11] 4,303,422

[45] Dec. 1, 1981

[54] FUEL FILTER

[75] Inventor: James G. Persinger, Hugoton, Kans.

[73] Assignee: Fuel Inc., Hugoton, Kans.

[21] Appl. No.: 152,385

[22] Filed: May 22, 1980

[51] Int. Cl.$^3$ .................... B01D 53/04; B01D 53/26
[52] U.S. Cl. .................................. 55/319; 55/389; 55/418
[58] Field of Search ................ 55/319, 387, 418, 389

[56] References Cited

U.S. PATENT DOCUMENTS

| 1,458,005 | 6/1923 | Rohrer | 55/319 |
| 2,129,490 | 9/1968 | Buchs | 55/418 |
| 2,973,327 | 2/1961 | Mitchell et al. | 55/389 X |
| 3,235,089 | 2/1966 | Burroughs | 55/389 X |
| 3,705,480 | 12/1972 | Wireman | 55/389 X |
| 3,772,857 | 11/1973 | Jackson et al. | 55/418 |
| 3,941,573 | 3/1976 | Chapel et al. | 55/389 X |

Primary Examiner—Robert H. Spitzer
Attorney, Agent, or Firm—Frank Frisenda, Jr.

[57] ABSTRACT

The invention provides an improved fuel filter for removing formation water, hydrogen sulfides, sulfur and other undesirable particulates from, for instance, a natural gas fuel supply. The improvement comprises a molecular sieve having a non-uniform diameter pelletized catalyst composed of an alkyl metal alumino silicate, combined with an inert binder. The catalyst accordingly resists powdering and supplies more free area between pellets, thus minimizing pressure drop through the molecular sieve portion of the filter. The improvement further comprises provision of tapered holes at the upper end of a tubular member contained within the lower portion of the filter. The tapered holes thus permit gaseous fuel flowing through the tubular member to undergo a rapid expansion, providing a more even distribution of fuel flow to the molecular sieve. The fuel, upon exiting the tubular member flows into a chamber concentric with the tubular member where entrained contaminants, in mass form, drop to the bottom of the chamber and are eliminated from the fuel supply.

3 Claims, 2 Drawing Figures

FUEL FILTER

BACKGROUND OF THE INVENTION

This invention relates to an improved fuel filter for removing formation water, hydrogen sulfides, sulfur, iron sulfide and other undesirable particulate matter from, for instance, a natural gas fuel supply.

A previously developed fuel filter, commercially available from Fuel, Inc. of Hugoton, Kans., the instant assignee, comprises a lower portion for removing formation water and particulates from a fuel supply and an upper portion comprising a chemically active molecular sieve. While generally effective in accomplishing its intended purpose, it has been found that the calcium catalyst of the sieve portion degraded too quickly and was subject to powdering. In this respect, if catalyst powder is allowed to fall from the sieve into an engine, it could render the engine inoperative.

Further, the catalyst of the aforementioned filter was pelletized in uniform diameter size. Thus, the fuel was subject to a relatively large pressure drop as the fuel flowed through the filter.

In a lower portion of the known filter, a T shaped portion was included for purposes of removing entrained contamination in mass form and formation water from the fuel supply. This T shaped portion was composed of a relatively poor acid resistance plastic.

Thus those skilled in the art have recognized a significant need for a more effective filter in removing formation water and contaminants from a fuel supply such as natural gas, particularly with respect to longer life expectancy for the catalyst of the molecular sieve and which would not cause such a large pressure drop as the fuel supply flowed through the filter. Moreover, a need for a more efficient filter portion for removing entrained contamination from the fuel supply was also recognized. The present invention fulfills this need.

SUMMARY OF THE INVENTION

The present invention provides an improved fuel filter for removing contaminants such as formation water, hydrogen sulfides, sulfur and other undesirable particulates from, for instance, a natural gas fuel supply.

The improvement comprises a molecular sieve having a non-uniform pelletized catalyst composed of an alkyl metal alumino silicate, combined with an inert binder contained within the filter. The catalyst accordingly resists powdering and supplies more free area between the pellets, thus minimizing pressure drop through the molecular sieve portion of the filter.

The improvement further comprises provision of tapered holes at the upper end of a tubular member contained within the lower portion of the filter. The improved filter includes a generally cylindrical body provided with upper and lower end caps, the lower end cap having a central aperture threaded to receive an inlet fuel supply pipe. Extending upwardly from the lower end cap aperture is a tubular member closed at its upper end by suitable means. A plurality of holes are provided in the sidewalls of the tubular member, the holes being tapered at about a 15° angle diverging toward the exterior surface of the tubular member. Accordingly, when gaseous fuel flows through the holes, the fuel undergoes an expansion thereby producing a more dispersed flow through the molecular sieve portion of the filter.

The above and other objects invented as of this invention will become apparent from the following more detailed description, when taken in conjunction with the accompanying drawing of an illustrative embodiment.

DESCRIPTION OF THE PREFERRED EMBODIMENT

The present invention provides an improved fuel filter for removing formation water, hydrogen sulfides, sulfur, iron sulfides and the like from a fuel supply such as natural gas, as it is derived from the ground. The removal of sulfur and sulfurous compound is desirable in order to reduce sulfur deposits on the internal parts of an engine and to reduce sulfur oxide emissions in exhaust gases.

Figure 1:
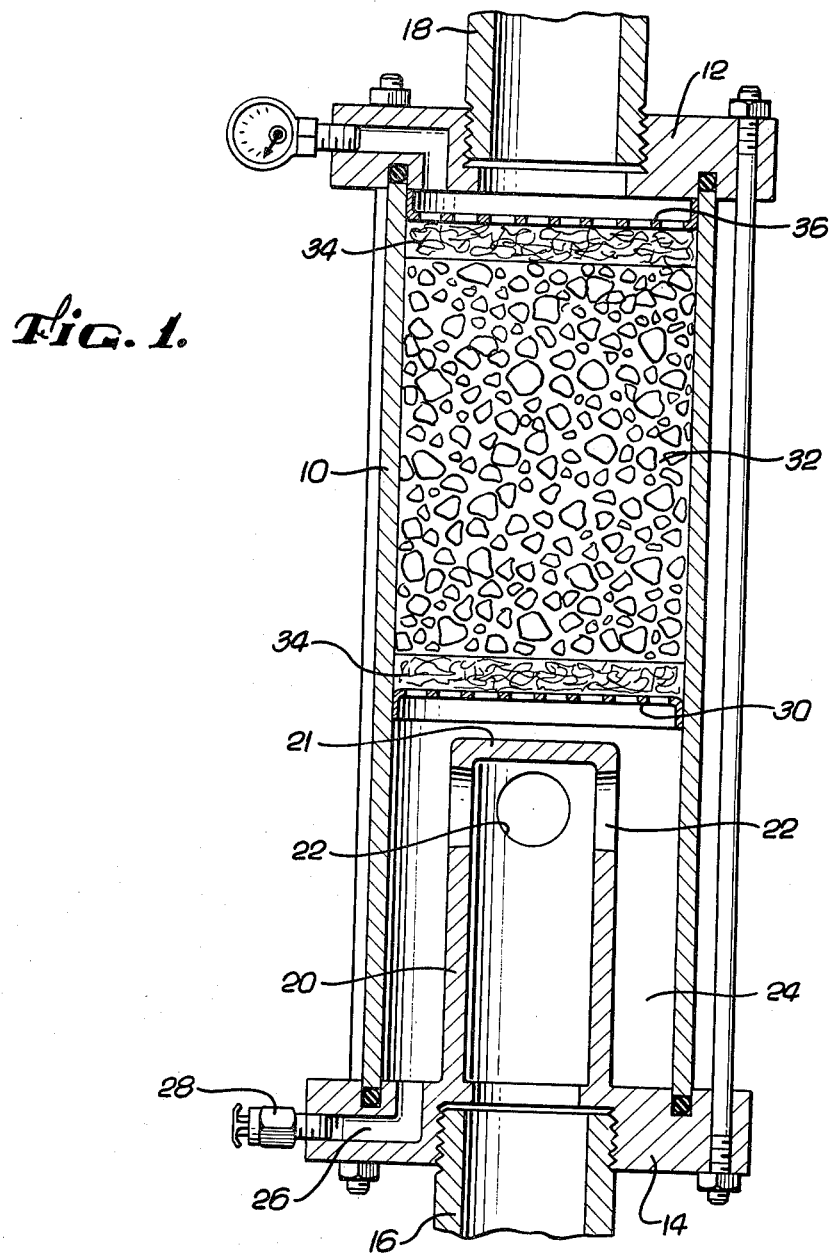
FIG. 1 is a front cross-sectional view showing an improved fuel filter in accordance with the present invention.

In accordance with the invention and with reference to FIG. 1, the improved filter includes a generally cylindrical body 10, provided with upper and lower end caps 12 and 14 respectively. The lower end cap 14 has a central aperture threaded to receive an inlet fuel supply pipe 16. The upper end cap 12 is also provided with a central aperture similarly threaded to receive an outlet fuel pipe 18 to an engine. Extending upwardly from the lower end cap aperture is a tubular member 20 closed at its upper end by suitable means 21 preferably integral with the member 20. A plurality of holes 22, preferably four, are provided in the side walls of the tubular member 20 to permit the gaseous fuel coming from the pipe 16 to discharge laterally. The fuel, upon entering the vertically mounted filter and flowing through holes 22 thus changes direction by approximately 90°, and enters into a chamber 24 concentric with the member 20 formed by the cylindrical body 10. This feature causes a sudden reduction in fuel flow velocity so that heavier particulate matter and accumulated formation water contained in the fuel is dropped in the bottom of the chamber 24. A drain line 26 disposed in the bottom end cap 14 is closed by a valve plug 28 to drain the water and particular matter from the chamber 24.

Above the chamber 24 is a screen 30 or similar member that supports a bed of chemically active molecular sieve material 32 which will be described herein in greater detail. Formation water which has not fallen to the bottom of the chamber 24 will accordingly be stopped by the molecular sieve material 32 and from there, fall back into the chamber 24 to be drained from the filter. The remaining impurities, such as hydrogen sulfide and the like, are absorbed in the molecular sieve material 32 and the remaining fuel supply then flows through the aperture in the upper end cap 12 to outlet fuel pipe 18.

The improved filter is especially suitable for cleaning natural gas before being supplied to an engine such as a compressor and will typically have 1½ inch to 2 inch inlet and outlet pipe, 16 and 18 respectively. Generally, working pressures through the filter will range from about 150–500 psi. Several filters may be installed in parallel, and/or the dimensions of components can be increased in size to accommodate larger volumes or higher working pressures.

When the chemically active molecular sieve material 32 of the fuel filter becomes ineffective with regard to removing contaminants, the expanded material, preferably in cartridge form, may be discarded and replaced with fresh material.

In more detail, the improvement in accordance with the present invention comprises a molecular sieve material 32 composed of a pelletized catalyst of alkyl metal alumino silicates combined with an inert binder to provide high absorption capacity, together with exceptional physical properties. When activated by heating, the crystalline structure of the catalyst is very porous and prefers water to any other molecule. The individual catalyst crystal is rigid and retains its shape at very high temperatures. This catalyst is commercially available under the trade name "Zeosorb" from Letcher and Associates, Lancaster, Calif. In general, the chemical formula of such catalyst is stated to be $(Ca, NaO_2).1.0\ Al_2O_3.5.1\ SiO_2.xH_2O$.

The catalyst pellets are of irregular size, for instance, having an average diameter from about 1/16 inch to ⅜ inch, to supply free area between pellets, thus minimizing pressure drop of the fuel supply through the filter.

Further, in accordance with the invention, fibrous padding 34 composed of an inert material such as fiberglass, is provided on top and bottom of the molecular sieve material 32. The fibrous padding 34 comprises two separate pads each about 2 microns thick. In position, the padding 34 prevents channeling of the gas supply flowing through the filter. Additionally, the padding will trap particulates and moisture from fuel flowing through the filter.

Above the top padding 34 a screen 36 is provided to contain the padding 34 and sieve material 32 within the cylindrical body 10.

Figure 2:
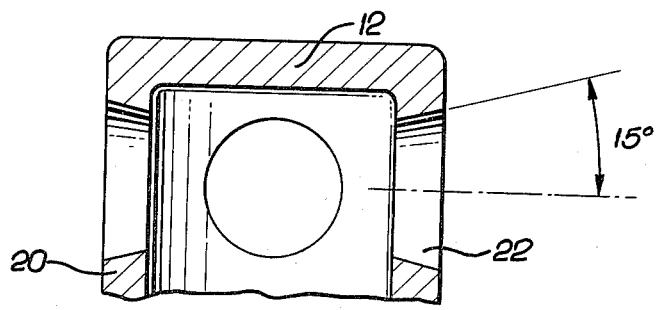
FIG. 2 is an enlarged fragmentary cross-sectional view of an upper portion of a tubular member contained within the filter provided with tapered holes to permit gaseous fuel flowing through the tubular member to undergo a rapid expansion in accordance with the invention.

The improvement to the lower portion of the filter depicted in FIG. 2 is the provision of tapered holes 22 to give a rapid expansion of fuel flow through the holes thereby producing a more dispersed flow through the sieve material 32. The holes are tapered at about a 15° angle diverging toward the exterior surface of the tubular member 20.

The tubular member 20 is composed of a corrosion resistant material, such as 6061 anodized aluminum, class 3 hardness.

When installed, the improved fuel filter removes up to 80% of entrained contaminants from the fuel supply, whereas the known fuel filter only removed 20% of such contaminants. The filter thus permits an engine to be operated on a fuel supply such as natural gas, as it flows from the ground. These filters may be used for treating gas for single and multiple cylinder pumping units, compressors, separators, heat treaters, and the like. A flow rate in the range of from about 5 scfm to about 250 scfm for fuel feed into the filter is generally desirable.

While a preferred form of the invention has been disclosed, it will be appreciated that modifications may be made therein without departing from the broad concept. Consequently this patent is not to be restricted to the particular form or arrangements of parts herein described and shown, except as limited by the claims.

I claim:

1. In a fuel filter device for removing contaminants comprising formation water, hydrogen sulfide, sulfur and iron sulfide, from a natural gas fuel supply, said filter including a cylindrical, hollow body having a bed of chemically active molecular sieve material disposed in an upper portion of said body and a tubular member extending upwardly from a central aperture provided in a lower end cap, and a chamber concentric with said member disposed in a lower portion of said body, the improvement comprising a plurality of holes provided in side walls of said tubular member said holes being tapered at about a 15° angle diverging toward the exterior surface of said tubular member, and said molecular sieve material comprising pellets of an alkyl metal amino silicate combined with an inert binder, wherein when natural gas fuel flows through said holes the fuel undergoes an expansion thereby producing a dispersed flow through said bed of chemically active molecular sieve material.

2. The filter of claim 1 wherein said tubular member is composed of anodized aluminum.

3. The filter of claim 1 wherein said pellets are irregularly shaped having an average non-uniform diameter in the range of from about 1/16 inch to about ⅜ inch.

* * * * *